United States Patent [19]

Wapner

[11] Patent Number: 5,504,685

[45] Date of Patent: Apr. 2, 1996

[54] METHOD AND APPARATUS FOR ROUTING AN UNDERWATER CABLE SYSTEM

[75] Inventor: Michael P. Wapner, Santa Barbara, Calif.

[73] Assignee: Sonatech, Inc., Santa Barbara, Calif.

[21] Appl. No.: 304,669

[22] Filed: Sep. 9, 1994

[51] Int. Cl.[6] .............................. G01N 3/30; G01V 1/38
[52] U.S. Cl. ..................... 364/443; 364/420; 73/82
[58] Field of Search .................. 364/449, 424.01, 364/420; 342/357, 457; 324/348; 73/81, 82, 84, 85; 367/2

[56] References Cited

U.S. PATENT DOCUMENTS

| | | | |
|---|---|---|---|
| 4,007,633 | 2/1974 | Thompson | 73/84 |
| 4,120,167 | 10/1978 | Denman et al. | 405/157 |
| 4,164,379 | 8/1979 | Denman | 405/158 |
| 4,186,373 | 1/1980 | Thompson | 367/131 |
| 5,444,670 | 8/1995 | Douglas | 367/90 |

OTHER PUBLICATIONS

Underwater Systems Design, *Developments in Cone Penetration Testing for Site Investigations*, by Dr. C. W. Swain, Fugro Limited, Feb./Mar. 1983.
Sonatech, Inc., Sounder, *Artic Tests Verify Performance of Penetrometer*, vol. 1, No. 1, Summer 1987.
Technical Report, R855, *Expendable Doppler Penetrometer: A Performance Evaluation*, by R. M. Beard, Jul. 1977.
Design News, *Seabed Penetrator Transmits Data by Wireless Signals*, Dec. 3, 1984.
Technical Report R905, *Expendable Doppler Penetrometer For Deep Ocean Sediment Strength Measurements*, by R. M. Beard, Mar. 1984.
Technical Report 242, *Interaction of Sound with the Ocean Bottom: A Three-Year Summary*, By H. E. Morris, E. L. Hamilton, H. P. Bucker, R. T. Bachman, Apr. 1978.

*Primary Examiner*—Michael Zanelli
*Attorney, Agent, or Firm*—Nydegger & Associates

[57] ABSTRACT

A system and method for identifying a route for excavation of an underwater trench on the seafloor includes a surface vessel, a plurality of penetrometers and an onboard computer. As the surface vessel plies along a proposed route for the underwater trench, penetrometers are launched from the vessel at selected launch points. Upon impact of a penetrometer with the seafloor, acoustic signals transmitted from the penetrometer during the impact event are analyzed by the onboard computer. From this computer analysis the seafloor at the impact point is classified as being in either a first state indicative of proceeding along the proposed route or a second state necessitating a deviation from the proposed route. Depending on the state of the seafloor and the number of deviations needed, the proposed route is returned to and followed, or a new proposed route is established. Data from the impact events are subsequently compiled to establish an actual route for excavation of the underwater trench.

18 Claims, 1 Drawing Sheet

METHOD AND APPARATUS FOR ROUTING AN UNDERWATER CABLE SYSTEM

FIELD OF THE INVENTION

The present invention pertains generally to systems and methods for excavating trenches on the surface of the earth. More particularly, the present invention pertains to a system and method for identifying an appropriate route for the excavation of a trench. The present invention is particularly, but not exclusively, useful for identifying a route for the excavation of an underwater trench across a seafloor.

BACKGROUND OF THE INVENTION

For many years underwater trenches have been needed for various applications. For instance, many examples can be given where undersea cable networks have been installed for communications purposes. Moreover, the need for such undersea cable networks will continue with even more urgency as new and improved cable networks with increased communications capabilities are developed to meet future communication needs.

A critical aspect of undersea trenching is the establishment of a suitable route. The selection of a proper route requires that obstacles, such as underwater mountain ranges and canyons, be avoided. In addition, it happens that the soil conditions encountered when excavating an underwater trench can be very important, even where canyons and mountain ranges are not encountered. For instance, the seabed, although flat, may comprise solid rock. On the other hand, the seabed may be extremely muddy and lack any real compaction. In cases where the seabed is largely rock, it may be impossible for the trenching equipment to properly excavate. Alternatively, in cases where the seafloor lacks adequate compaction, there may be inadequate support for the trenching equipment or the trench itself may collapse subsequent to the trenching operation.

In the past, information about sea floor soil conditions was generally obtained by collection of core samples. The collection of core samples involved repeatedly releasing and retrieving a coring penetrometer. The coring penetrometer would collect a sample of the seafloor at the point of impact and the sample would be analyzed after retrieval of the coring penetrometer. Unfortunately, the retrieval of the coring penetrometer and the subsequent analysis of the seafloor sample were time consuming procedures. In particular, the use of the coring penetrometer required that the release vessel loiter at each release point while the coring penetrometer was released and recaptured. As a result, the establishment of a suitable route for an undersea trench has generally been an arduous and expensive process.

In light of the above, it is an object of the present invention to provide a system and method for identifying a route for the excavation of an underwater trench which verifies whether a proposed route is appropriate, and which replots the proposed route as necessary. Another object of the present invention is to provide a system and method for identifying a route for the excavation of an underwater trench which continuously identifies penetrometer launch points along a proposed route according to data received at prior launch points. Still another object of the present invention is to provide a system and method for identifying a route for excavation of an underwater trench which minimizes the time spent at each penetrometer launch point. Still another object of the present invention is to provide a system and method for identifying a route for excavation of an underwater trench which provides for onboard analysis of data collected at a launch site, and which integrates data collected from multiple launch sites to establish an actual route for an underwater trench. Yet another object of the present invention is to provide a system and method for identifying a route for excavation of an underwater trench which is simple to use, easy to operate and comparatively cost effective.

SUMMARY OF THE PREFERRED EMBODIMENT OF THE INVENTION

A system and method for identifying a route for the excavation of an underwater trench on the seafloor includes a surface vessel, a plurality of penetrometers, and a computer onboard the surface vessel. The penetrometers are launchable into the ocean from the surface vessel and emit an acoustic signal during descent and impact with the seafloor which is transmitted to the onboard computer. This acoustic signal contains information about the characteristics of the seafloor, to include its composition and compaction.

For purposes of the present invention, the onboard computer can be preprogrammed with a proposed route for the underwater trench. Also, the onboard computer can be linked with the global positioning satellite (GPS) system so that each launch point where a penetrometer is dropped into the ocean can be accurately plotted.

In the operation of the present invention, a proposed route for the underwater trench is determined. The surface vessel then begins sailing along the proposed route, and at a predetermined point on the proposed route a penetrometer is launched into the ocean. This initial launch point is plotted, preferably using GPS, and the acoustic signal transmitted from the penetrometer upon its impact with the seafloor is associated with the launch point location.

The acoustic signal transmitted from the penetrometer during impact is immediately analyzed by the onboard computer to determine the characteristics of the seafloor at the particular launch point. Based on these characteristics, the onboard computer classifies the condition of the seafloor at the launch point into either a first state or a second state. For a first state condition, the seafloor is determined to be suitable for excavation of the trench and the surface vessel then continues along the proposed route to a subsequent launch point where the process is repeated with the launching of another penetrometer. For a second state condition, however, the seafloor is determined to be unsuitable for excavation of the trench and the surface vessel is required to make a deviation from the proposed route.

A deviation from the proposed route can be accomplished in several ways. In all cases, however, a deviation is made according to the best information that is available about the topography of the seafloor. One way by which a deviation can be executed is to proceed to a subsequent launch point which is located off the proposed route on a line that is generally perpendicular to the proposed route. If the subsequent launch point is in a first state condition, it is preferable to then return to the originally proposed route for subsequent launch points. If a sequence of deviations are required, however, it may be necessary to replot the proposed route, or at least a portion thereof.

In cases where additional accuracy is required, a coring penetrometer may be released at any launch point. The coring penetrometer is then retrieved and the soil sample carried by the coring penetrometer is analyzed to verify the accuracy of the acoustic penetrometer. This correlation procedure is particularly useful at the initial launch point.

As data from various launch points are collected and analyzed, the data is collated and used to verify or reject locations on the proposed route as suitable for the underwater trench. With verified locations, however, an actual suitable route for the trench can be identified. Consequently, during a single voyage of a surface vessel, a suitable and feasible route for an underwater trench can be identified. Further, the information required for excavating the underwater trench is immediately available.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENTS

Figure 1:
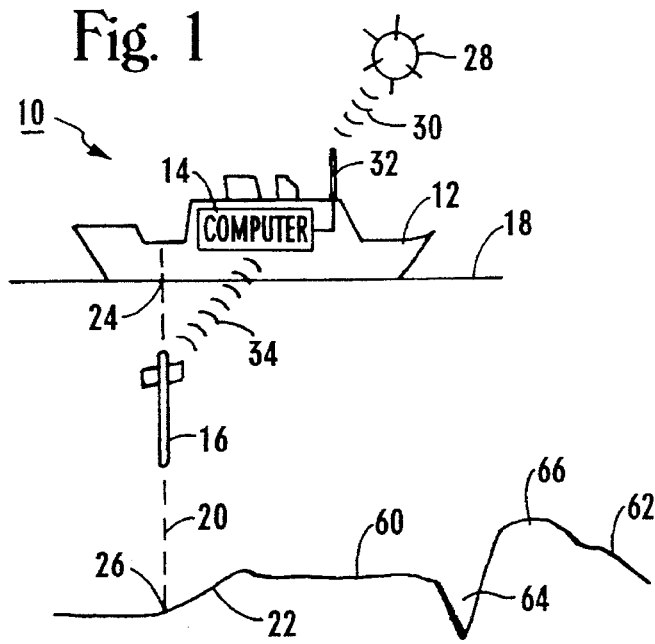
FIG. 1 is a schematic drawing with the components of the present invention shown in their operative relationship and environment.

Referring initially to FIG. 1 a system according to the present invention is shown and generally designated 10. As shown, the basic components of the system 10 include a surface vessel 12, a computer 14 which is located onboard the vessel 12, and a penetrometer 16. For purposes of the present invention, the penetrometer 16 is launched from the vessel 12 on the surface of the ocean 18 for descent along a path 20 toward seafloor 22. For all practical purposes, the path 20 can be considered to be substantially vertical. Therefore, the launch point 24 where penetrometer 16 enters the water is directly above the impact point 26 where the penetrometer hits the seafloor 22.

In accordance with the present invention, the surface vessel 12 can be of any type which can carry the necessary number of penetrometers 16 (which may be many) and the requisite electronic components for operation of the computer 14. Further, the penetrometer 16 is preferably of a type disclosed in copending application Ser. No. 08/293,988 for an invention entitled "Moduler Penetrometer", which is incorporated herein by reference, and which is assigned to the same assignee as the present invention.

FIG. 1 also shows that the system 10 may be used in combination with a GPS satellite 28. For this embodiment, signals 30 from the GPS satellite 28 are received by an antenna 32 which is onboard surface vessel 12. From the antenna 32, the signals 30 are fed to computer 14 where they are used in a manner well known to the art to precisely identify the global position of launch point 24 of penetrometer 16.

In addition to the signals 30 from GPS satellite 28, signals 34 from penetrometer 16 are also fed as input to computer 14. Preferably, the signals 34 are acoustic signals which can be used to generate velocity data for penetrometer 16. In turn, the velocity data from penetrometer 16 can be effectively used to analyze the soil characteristics, including composition and compaction, of seafloor 22 at impact point 26. Preferably, the method for converting signals 34 into useable data concerning soil characteristics of the seafloor 22 is a method as disclosed in a copending application Ser. No. 08/303,051, now U.S. Pat. No. 5,444,670 entitled "Method And Apparatus For Determining Soil Strength From Doppler-Shifted Acoustic Signatures", which is incorporated herein by reference, and which is assigned to the same assignee as the present invention.

A number of different methodologies may be used with system 10 of the present invention to identify a route for excavation of an underwater trench. One possible method for using the system 10 of the present invention is illustrated by the step/logic flow chart of FIG. 2 and is generally designated 40. The start of method 40 is indicated by the oval 42 and is accomplished by launching a penetrometer 16 from the surface vessel 12 at a launch point 24. This action is shown by the block 44 in FIG. 2. As the penetrometer 16 descends into the sea along path 20, block 46 indicates that signals 34 are transmitted from the penetrometer 16 and fed into computer 14. As stated above, the signals 34 include information about soil characteristics at impact point 26 where penetrometer 16 comes to rest on the seafloor 22. Decision point 48 indicates that computer 14 then immediately analyzes signals 34 to determine whether the soil characteristics require classification of the impact point 26 into either a first state or a second state.

Classification of the seafloor 22 at impact point 26 as being in a first state condition indicates that the seafloor 22 at impact point 26 is suitable for excavation of an underwater trench. Preferably, but depending on the particular hydrodynamic and structural configuration of penetrometer 16, for a first state condition it is desirable for the penetrometer 16 to penetrate seafloor 22 through a distance of approximately one to four feet. Penetration distances substantially less than one foot may indicate that the seafloor 22 is too hard for excavation. On the other hand, penetration distances substantially more than four feet may indicate that the seafloor 22 is not capable of supporting the trenching equipment. In either case, if the penetration distance is too deep or too shallow, the condition is unsuitable for excavation of an underwater trench. For purposes of the present invention, a condition wherein the seafloor 22 is unsuitable for the excavation of a trench is classified as a second state.

Figure 2:
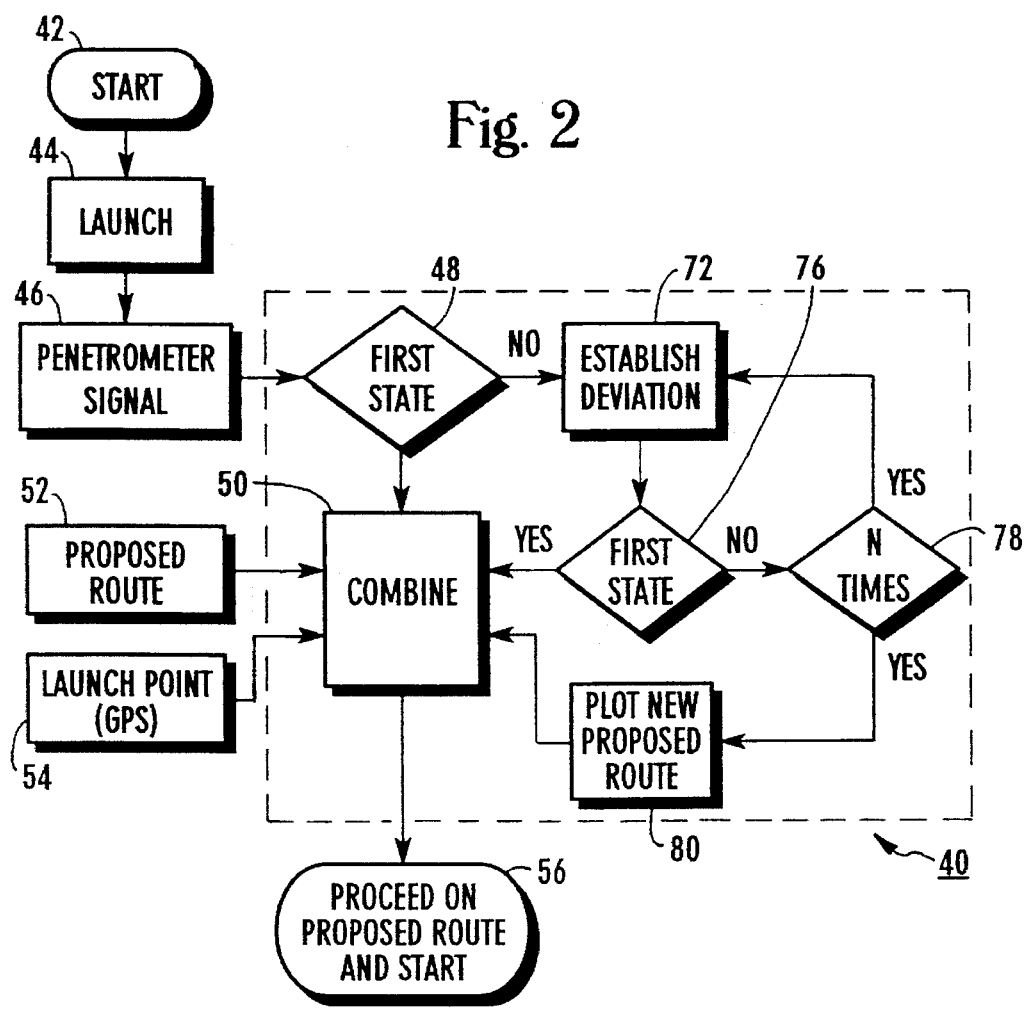
FIG. 2 is a flow chart of the steps and logic involved in the operation of the present invention.

Decision point 48 of method 40 in FIG. 2 also indicates that if seafloor 22 is determined to be in a first state, the next step of method 40 is to combine this determination of state with other information. Specifically, block 50 shows that information about the proposed route of the underwater trench (block 52) and information about the launch point location (block 54) are combined with the first state condition to establish the fact that the particular portion of seafloor 22 in the vicinity of launch point 24 is suitable for excavation of the actual underwater trench. With this information, as indicated by oval 56 of method 40, surface vessel 12 proceeds to a subsequent launch point 24' on the proposed route where system 10 and method 40 continue to verify and identify a route for the underwater trench by launching another penetrometer 16.

Figure 3:
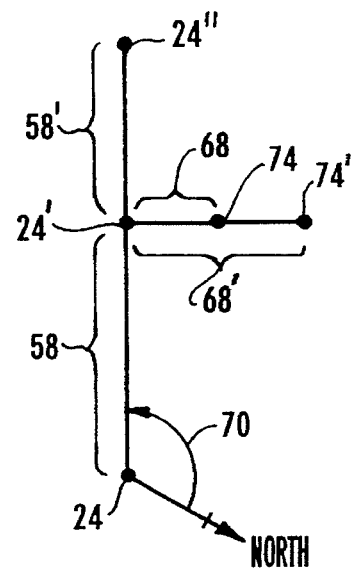
FIG. 3 is an exemplary depiction of a proposed route and a possible deviation therefrom according to the present invention.

The distance 58 that a surface vessel 12 travels from one launch point 24 to a subsequent launch point 24' is variable and will depend in large part on the topography of the seafloor 22. This can, perhaps, be best appreciated by cross referencing between FIG. 1 and FIG. 3. In the event it is known that the seafloor 22 is generally flat and has generally uniform consistency, such as shown in the area 60 in FIG. 1, then the distance 58 from launch point 24 to launch point 24' can be substantial. On the other hand, if the topography of seafloor 22 is on an incline 62, or if the seafloor 22 is known to incorporate a number of different bottom types, a shorter distance than distance 58, such as the distance 58' shown between launch point 24' and launch point 24" in FIG. 3, may be more appropriate. Further, FIG. 3 shows that the distance 58 taken from launch point 24 is in a direction determined by the angle 70. Over any distance 58 there is, however, the ever present possibility that seafloor 22 along the proposed route may be a canyon 64 or a mountain 66. Such topographical features, like any second state condition, are to be avoided. Where avoidance is necessary, a deviation 68 is in order.

Block 72 in FIG. 2 indicates that if a first state is not classified for the seafloor 22 at an impact point 26, i.e. the impact point 26 is in a second state condition, then there is a need to establish a deviation 68 from the proposed route for a subsequent launch point 74. Specifically, as shown in FIG. 3, a launch point 74 is shown on a line which is substantially at a right angle (90°) from the proposed route. While subsequent launch point 74 is shown to the right of the proposed route, it could as easily have been to the left. In either case, the distance of the deviation 68 is somewhat arbitrary. For ease of execution, however, there should be some consistency.

One method for instituting a deviation 68 is to establish a set distance from the proposed route for the launch point 74. As indicated in FIG. 3, a deviation 68 from the proposed route is executed when the soil condition at the last launch point 24 on the proposed route (impact point 26) is not in a first state. The deviation 68 then takes surface vessel 12 to the launch point 74 which is off the proposed route. The decision point 76 in FIG. 3 then requires a determination as to whether the soil conditions corresponding to launch point 74 are in a first condition. This, of course, requires the launching of another penetrometer 16 and a repetition of the process described above. Decision point 76 also indicates that if the soil condition under launch point 74 is in a first state, this information is combined with launch point position data 54 obtained from signals 30. Then, as indicated by oval 56, the surface vessel should return to the proposed route and proceed with method 40.

In the event the soil condition of seafloor 22 under launch point 74 is in a second state, then a further deviation is required. One course of action would be to simply try a penetrometer launch at a deviation 68 on the other (left) side of the proposed route. Another is to proceed further from the proposed route on the same side. For this latter possibility, the decision point 78 of method 40 requires an inquiry into the number of times (n) there have been previous deviations. If there have been any previous deviations 68 then another deviation, such as deviation 68' shown in FIG. 3 is established. For example, if there has been one previous deviation, and the result has been a second state classification for the seafloor 22 at the launch point 74, then n=1 and the deviation 68' can be established as a set distance which is equal to n times a predetermined distance. As shown in FIG. 3, this would take the surface vessel 12 to the subsequent launch point 74' where method 40 would again be started.

In the event there have been at least two deviations 68 and 68' (n=1), where n is the number of previous unsuccessful deviations, then block 80 of method 40 indicates a new proposed route can be plotted. For purposes of the present invention, this may mean that either the entire route is to be replotted or, as a less drastic measure, only a portion of the route is to be replotted. In any event, it is the intent of the present invention to proceed and collect a significant number of launch points 24/74 which can be used to establish an actual route for the underwater trench from its intended beginning to its intended end.

While the particular system and method for using a surface vessel to identify a route for excavation of an underwater trench on the seafloor as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A method for using a surface vessel to identify a route for excavation of an underwater trench on the seafloor which comprises the steps of:

plotting a proposed route for said trench along the seafloor;

locating a launch point;

launching a penetrometer from said surface vessel at said launch point, said penetrometer generating signals during impact of said penetrometer at an impact point on the seafloor;

analyzing said signals for classification of said seafloor at said impact point into a first state or a second state;

proceeding to a location on said proposed route to establish a subsequent launch point when said seafloor at said impact point is in said first state;

establishing a deviation from said proposed route for a subsequent launch point when said sea floor at said impact point is in said second state; and repeating, as necessary, said steps of launching, analyzing, proceeding and establishing.

2. A method as recited in claim 1 wherein said proceeding step is accomplished by moving said surface vessel through a distance and in a direction from said launch point.

3. A method as recited in claim 1 wherein said step of establishing a deviation further comprises the steps of:

assigning a sequence number to said deviation; and locating said subsequent launch point at a set distance from said proposed route according to said sequence number.

4. A method as recited in claim 3 wherein said set distance is measured along a line from said launch point substantially perpendicular to said proposed route.

5. A method as recited in claim 4 wherein said sequence number is equal to the number of prior said deviations and said set distance is a sequence number multiple of a predetermined distance.

6. A method as recited in claim 1 further comprising the step of corresponding said launch point with said impact point.

7. A method as recited in claim 1 further comprising the step of mapping an actual route for said underwater trench according to impact points analyzed as having a first state.

8. A method as recited in claim 1 wherein said first state corresponds to seafloor characteristics which are conducive to excavation of said underwater trench and said second state corresponds to seafloor characteristics which are not conducive to excavation of said underwater trench.

9. A method as recited in claim 1 wherein an initial launch point is located on said proposed route.

10. A method as recited in claim 1 wherein said locating step is accomplished using the global positioning satellite system.

11. A method as recited in claim 1 wherein said signals generated by said penetrometer are acoustic signals.

12. A method as recited in claim 1 further comprising the step of replotting said proposed route based on analysis of said second state.

13. A system for identifying a route for excavation of an underwater trench on the seafloor which comprises:
 a surface vessel;
 a plurality of penetrometers launchable from said surface vessel, each of said penetrometers generating acoustic signals during impact of said penetrometer at an impact point on the seafloor;
 a computer positioned on said surface vessel, said computer being preprogrammed with a proposed route for said trench along the seafloor, said computer being programmable with a launch point whenever one said penetrometer is launched from said surface vessel and, said computer including means for analyzing said signals for classification of said seafloor at said impact point into a first state indicative of proceeding to a location on said proposed route to establish a subsequent launch point or a second state indicative of establishing a deviation from said proposed route to establish a subsequent launch point.

14. A system as recited in claim 13 wherein said surface vessel is moved through a distance and in a direction from said launch point after launching one said penetrometer and wherein said distance is based on analysis of said first state.

15. A system as recited in claim 14 wherein said deviation is assigned a sequence number and said subsequent launch point is at a set distance from said proposed route according to said sequence number, said sequence number being equal to the number of prior said deviations, and said set distance being a multiple of said sequence number and a predetermined distance and measured along a line from said launch point substantially perpendicular to said proposed route.

16. A system as recited in claim 15 wherein said computer further comprises:
 means electronically connectable with said computer for inputting said launch point based on data from the global positioning satellite system; and
 means for corresponding said launch point with said impact point.

17. A system as recited in claim 16 wherein said computer further comprises means for mapping an actual route for said underwater trench according to impact points analyzed as having said first state.

18. A system as recited in claim 17 wherein said penetrometer is configured to penetrate less than four feet into the seafloor for seafloor characteristics corresponding to said first state.

* * * * *